(12) United States Patent
Kaval (10) Patent No.: US 9,223,050 B2
(45) Date of Patent: *Dec. 29, 2015

(54) X-RAY IMAGING SYSTEM HAVING IMPROVED MOBILITY

(71) Applicant: Rapiscan Systems, Inc., Torrance, CA (US)

(72) Inventor: Brian Kaval, Long Beach, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/268,112

(22) Filed: May 2, 2014

(65) Prior Publication Data

US 2015/0285940 A1 Oct. 8, 2015

Related U.S. Application Data

(63) Continuation of application No. 13/248,096, filed on Sep. 29, 2011, now Pat. No. 8,750,452, which is a continuation of application No. 12/848,985, filed on Aug. 2, 2010, now Pat. No. 8,054,938, which is a continuation of application No. 12/275,386, filed on Nov. 21, 2008, now Pat. No. 7,783,005, which is a continuation of application No. 11/404,386, filed on Apr. 14, 2006, now Pat. No. 7,471,764.

(60) Provisional application No. 60/671,900, filed on Apr. 15, 2005.

(51) Int. Cl.
*G01V 5/00* (2006.01)

(52) U.S. Cl.
CPC ................... *G01V 5/0016* (2013.01)

(58) Field of Classification Search
CPC .................... G01N 23/04; G01V 5/0016
USPC ........................................................... 378/57
See application file for complete search history.

(56) References Cited

U.S. PATENT DOCUMENTS

| 2,420,845 | A |   | 5/1947 | Slack |       |
|-----------|---|---|--------|-------|-------|
| 2,457,841 | A | * | 1/1949 | Smith et al. | 220/1.5 |
| 2,636,619 | A |   | 4/1953 | Alexander |   |
| 2,831,123 | A |   | 4/1958 | Daly |       |

(Continued)

FOREIGN PATENT DOCUMENTS

| DE | 2729353 A1 | 1/1979 |
| DE | 3214910 A1 | 5/1983 |

(Continued)

OTHER PUBLICATIONS

US 5,987,079, 11/1999, Salasoo, (withdrawn).

(Continued)

*Primary Examiner* — Glen Kao
*Assistant Examiner* — Chih-Cheng Kao
(74) *Attorney, Agent, or Firm* — Novel IP (57) ABSTRACT

It is an object of the present application to provide a radiation inspection system, such as an X-ray system, that can operate efficiently even in inclement weather conditions while being highly mobile. Thus the improved inspection system of the present application is capable of operating in high temperature and corrosive environments and is designed to withstand moisture, dirt and/or dust from the articles of inspection as well.

12 Claims, 4 Drawing Sheets

(56) References Cited

U.S. PATENT DOCUMENTS

| | | |
|---|---|---|
| 2,885,069 A | 5/1959 | Bowen |
| 2,952,790 A | 9/1960 | Steen |
| 2,971,433 A | 2/1961 | Akin |
| 3,070,399 A | 12/1962 | Bartlett |
| 3,073,960 A | 1/1963 | Guentner |
| 3,146,349 A | 8/1964 | Jordan |
| 3,239,706 A | 3/1966 | Farrell |
| 3,275,831 A | 9/1966 | Martin |
| 3,374,355 A | 3/1968 | Parratt |
| 3,458,026 A | 7/1969 | Lauzon |
| 3,485,339 A | 12/1969 | Miller |
| 3,676,783 A | 7/1972 | Kinbara |
| 3,766,387 A | 10/1973 | Heffan |
| 3,767,850 A | 10/1973 | McMillian |
| 3,768,645 A | 10/1973 | Conway |
| 3,770,955 A | 11/1973 | Tomita |
| 3,784,837 A | 1/1974 | Holmstrom |
| 3,837,502 A | 9/1974 | Hornagold |
| RE28,544 E | 9/1975 | Stein |
| 3,904,923 A | 9/1975 | Schwartz |
| 3,919,467 A | 11/1975 | Peugeot |
| 3,955,678 A | 5/1976 | Moyer |
| 3,961,186 A | 6/1976 | Leunbach |
| 3,980,889 A | 9/1976 | Haas |
| 4,020,346 A * | 4/1977 | Dennis ............................ 378/57 |
| 4,047,035 A | 9/1977 | Dennhoven |
| 4,057,725 A | 11/1977 | Wagner |
| 4,064,440 A | 12/1977 | Roder |
| 4,105,922 A | 8/1978 | Lambert |
| 4,139,771 A | 2/1979 | Dennhoven |
| 4,164,138 A | 8/1979 | Burkhart |
| 4,210,811 A | 7/1980 | Dennhoven |
| 4,216,499 A | 8/1980 | Kunze |
| 4,228,353 A | 10/1980 | Johnson |
| 4,259,721 A | 3/1981 | Kuznia |
| 4,266,425 A | 5/1981 | Allport |
| 4,274,005 A | 6/1981 | Yamamura |
| 4,340,816 A | 7/1982 | Schott |
| 4,352,021 A | 9/1982 | Boyd |
| 4,366,382 A | 12/1982 | Kotowski |
| 4,380,817 A | 4/1983 | Harding |
| 4,430,568 A | 2/1984 | Yoshida |
| 4,468,802 A | 8/1984 | Friedel |
| 4,481,403 A | 11/1984 | Del Monte |
| 4,501,011 A | 2/1985 | Hauck |
| 4,525,854 A | 6/1985 | Molbert |
| 4,563,707 A | 1/1986 | Kishida |
| 4,566,113 A | 1/1986 | Doenges |
| 4,599,740 A | 7/1986 | Cable |
| 4,626,688 A | 12/1986 | Barnes |
| 4,641,330 A | 2/1987 | Herwig |
| 4,672,649 A | 6/1987 | Rutt |
| 4,675,890 A | 6/1987 | Plessis |
| 4,709,382 A | 11/1987 | Sones |
| 4,736,401 A | 4/1988 | Donges |
| 4,752,948 A | 6/1988 | MacMahon |
| 4,788,704 A | 11/1988 | Donges |
| 4,799,247 A | 1/1989 | Annis |
| 4,809,312 A | 2/1989 | Annis |
| 4,809,857 A | 3/1989 | Steuck |
| 4,817,123 A | 3/1989 | Sones |
| 4,825,454 A | 4/1989 | Annis |
| 4,831,260 A | 5/1989 | DiBianca |
| RE32,961 E | 6/1989 | Wagner |
| 4,853,595 A | 8/1989 | Alfano |
| 4,864,142 A | 9/1989 | Gomberg |
| 4,866,439 A | 9/1989 | Kraus |
| 4,866,745 A | 9/1989 | Akai |
| 4,868,856 A | 9/1989 | Frith |
| 4,870,670 A | 9/1989 | Geus |
| 4,872,188 A | 10/1989 | Lauro |
| 4,879,735 A * | 11/1989 | Owens ............................ 378/57 |
| 4,884,289 A | 11/1989 | Glockmann et al. |
| 4,887,604 A | 12/1989 | Shefer |
| 4,979,137 A | 12/1990 | Gerstenfeld |
| 4,979,202 A | 12/1990 | Siczek |
| 4,987,584 A | 1/1991 | Doenges |
| 4,991,189 A | 2/1991 | Boomgaarden |
| 4,991,708 A | 2/1991 | Francioni |
| 5,006,299 A | 4/1991 | Gozani |
| 5,014,293 A | 5/1991 | Boyd |
| 5,022,062 A | 6/1991 | Annis |
| 5,033,106 A | 7/1991 | Kita |
| 5,040,199 A | 8/1991 | Stein |
| 5,065,418 A | 11/1991 | Bermbach et al. |
| 5,067,145 A | 11/1991 | Siczek |
| 5,076,993 A | 12/1991 | Sawa |
| 5,086,300 A | 2/1992 | Ashmore |
| 5,091,924 A | 2/1992 | Bermbach |
| 5,092,451 A | 3/1992 | Jones |
| 5,097,939 A | 3/1992 | Shanklin |
| 5,098,640 A | 3/1992 | Gozani |
| 5,114,662 A | 5/1992 | Gozani |
| 5,144,191 A | 9/1992 | Jones |
| 5,179,581 A | 1/1993 | Annis |
| 5,181,234 A | 1/1993 | Smith |
| 5,182,764 A | 1/1993 | Peschmann |
| 5,185,778 A | 2/1993 | Magram |
| 5,202,932 A | 4/1993 | Cambier |
| 5,221,843 A | 6/1993 | Alvarez |
| 5,224,144 A | 6/1993 | Annis |
| 5,237,598 A | 8/1993 | Albert |
| 5,243,693 A | 9/1993 | Maron |
| 5,247,556 A | 9/1993 | Eckert |
| 5,247,561 A | 9/1993 | Kotowski |
| 5,253,283 A | 10/1993 | Annis |
| 5,259,014 A | 11/1993 | Brettschneider |
| 5,260,983 A | 11/1993 | Ono et al. |
| 5,272,627 A | 12/1993 | Maschhoff |
| 5,313,511 A | 5/1994 | Annis |
| 5,319,547 A | 6/1994 | Krug |
| 5,321,271 A | 6/1994 | Schonberg |
| 5,341,916 A | 8/1994 | Doane |
| 5,367,552 A | 11/1994 | Peschmann |
| 5,379,334 A | 1/1995 | Zimmer |
| 5,394,454 A | 2/1995 | Harding |
| 5,410,156 A | 4/1995 | Miller |
| 5,412,702 A | 5/1995 | Sata |
| 5,418,372 A | 5/1995 | Schonberg |
| 5,430,787 A | 7/1995 | Norton |
| 5,467,377 A | 11/1995 | Dawson |
| 5,490,196 A | 2/1996 | Rudich |
| 5,490,218 A | 2/1996 | Krug |
| 5,493,596 A | 2/1996 | Annis |
| 5,505,291 A | 4/1996 | Huang |
| 5,511,104 A | 4/1996 | Mueller |
| 5,524,133 A | 6/1996 | Neale |
| 5,548,123 A | 8/1996 | Perez-Mendez |
| 5,557,108 A | 9/1996 | Tumer |
| 5,590,057 A | 12/1996 | Fletcher |
| 5,600,303 A | 2/1997 | Husseiny |
| 5,600,700 A | 2/1997 | Krug |
| 5,604,778 A | 2/1997 | Polacin |
| 5,606,167 A | 2/1997 | Miller |
| 5,633,907 A | 5/1997 | Gravelle |
| 5,634,551 A | 6/1997 | Francioni |
| 5,638,420 A | 6/1997 | Armistead |
| 5,638,817 A | 6/1997 | Morgan |
| 5,642,393 A | 6/1997 | Krug |
| 5,642,394 A | 6/1997 | Rothschild |
| 5,660,549 A | 8/1997 | Witt |
| 5,661,377 A | 8/1997 | Mishin |
| 5,661,774 A | 8/1997 | Gordon |
| 5,666,393 A | 9/1997 | Annis |
| 5,687,210 A | 11/1997 | Maitrejean |
| 5,689,541 A | 11/1997 | Schardt |
| 5,692,028 A | 11/1997 | Geus |
| 5,692,029 A | 11/1997 | Husseiny |
| 5,696,806 A | 12/1997 | Grodzins |
| 5,712,926 A | 1/1998 | Eberhard |
| 5,738,202 A | 4/1998 | Ydoate |
| 5,744,919 A | 4/1998 | Mishin |
| 5,751,837 A | 5/1998 | Watanabe |
| 5,763,886 A | 6/1998 | Schulte |

(56) References Cited

U.S. PATENT DOCUMENTS

| | | | |
|---|---|---|---|
| 5,764,683 A | 6/1998 | Swift |
| 5,768,334 A | 6/1998 | Maitrejean |
| 5,787,145 A | 7/1998 | Geus |
| 5,796,802 A | 8/1998 | Gordon |
| 5,805,660 A | 9/1998 | Perion |
| 5,818,897 A | 10/1998 | Gordon |
| 5,838,758 A | 11/1998 | Krug |
| 5,838,759 A | 11/1998 | Armistead |
| 5,841,831 A | 11/1998 | Hell |
| 5,859,891 A | 1/1999 | Hibbard |
| 5,870,449 A | 2/1999 | Lee |
| 5,881,122 A | 3/1999 | Crawford |
| 5,882,206 A | 3/1999 | Gillio |
| 5,887,047 A | 3/1999 | Bailey |
| 5,901,198 A | 5/1999 | Crawford |
| 5,903,008 A | 5/1999 | Li |
| 5,903,623 A | 5/1999 | Swift |
| 5,905,806 A | 5/1999 | Eberhard |
| 5,909,477 A | 6/1999 | Crawford |
| 5,909,478 A | 6/1999 | Polichar |
| 5,910,973 A | 6/1999 | Grodzins |
| 5,930,326 A | 7/1999 | Rothschild |
| 5,936,247 A | 8/1999 | Lange |
| 5,940,468 A | 8/1999 | Huang |
| 5,949,811 A | 9/1999 | Baba |
| 5,949,842 A | 9/1999 | Schafer |
| 5,963,211 A | 10/1999 | Oikawa |
| 5,966,422 A | 10/1999 | Dafni |
| 5,970,113 A * | 10/1999 | Crawford et al. ............... 378/19 |
| 5,974,111 A | 10/1999 | Krug |
| 5,982,843 A | 11/1999 | Bailey |
| 5,987,097 A | 11/1999 | Salasoo |
| 6,018,562 A | 1/2000 | Willson |
| 6,021,174 A | 2/2000 | Campbell |
| 6,026,143 A | 2/2000 | Simanovsky |
| 6,026,171 A | 2/2000 | Hiraoglu |
| 6,031,888 A | 2/2000 | Ivan |
| 6,031,890 A | 2/2000 | Bermbach |
| 6,032,808 A | 3/2000 | Henson |
| 6,035,014 A | 3/2000 | Hiraoglu |
| 6,037,597 A | 3/2000 | Karavolos |
| 6,044,353 A | 3/2000 | Pugliese |
| 6,056,671 A | 5/2000 | Marmer |
| 6,058,158 A | 5/2000 | Eiler |
| 6,067,344 A | 5/2000 | Grodzins |
| 6,067,366 A | 5/2000 | Simanovsky |
| 6,073,751 A | 6/2000 | Worzischek |
| 6,075,871 A | 6/2000 | Simanovsky |
| 6,076,400 A | 6/2000 | Bechwati |
| 6,078,642 A | 6/2000 | Simanovsky |
| 6,081,580 A | 6/2000 | Grodzins |
| 6,088,423 A | 7/2000 | Krug |
| 6,091,795 A | 7/2000 | Schafer |
| 6,094,472 A | 7/2000 | Smith |
| 6,108,396 A | 8/2000 | Bechwati |
| 6,111,974 A | 8/2000 | Hiraoglu |
| 6,118,852 A | 9/2000 | Rogers |
| 6,122,343 A | 9/2000 | Pidcock |
| 6,128,365 A | 10/2000 | Bechwati |
| 6,134,299 A | 10/2000 | Artig |
| 6,137,895 A | 10/2000 | Al-Sheikh |
| 6,149,592 A | 11/2000 | Yanof |
| 6,151,381 A | 11/2000 | Grodzins |
| 6,163,591 A | 12/2000 | Benjamin |
| 6,181,765 B1 | 1/2001 | Sribar |
| 6,183,139 B1 | 2/2001 | Solomon |
| 6,185,272 B1 | 2/2001 | Hiraoglu |
| 6,188,745 B1 | 2/2001 | Gordon |
| 6,188,747 B1 | 2/2001 | Geus |
| 6,192,101 B1 | 2/2001 | Grodzins |
| 6,192,104 B1 | 2/2001 | Adams |
| 6,195,413 B1 | 2/2001 | Geus |
| 6,195,444 B1 | 2/2001 | Simanovsky |
| 6,198,795 B1 | 3/2001 | Naumann |
| 6,200,024 B1 | 3/2001 | Negrelli |
| 6,212,251 B1 | 4/2001 | Tomura |
| 6,216,540 B1 | 4/2001 | Nelson |
| 6,218,943 B1 | 4/2001 | Ellenbogen |
| 6,236,709 B1 | 5/2001 | Perry |
| 6,236,712 B1 | 5/2001 | Tomasetti |
| 6,246,320 B1 | 6/2001 | Monroe |
| 6,249,567 B1 | 6/2001 | Rothschild |
| 6,252,929 B1 | 6/2001 | Swift |
| 6,256,369 B1 | 7/2001 | Lai |
| 6,256,404 B1 | 7/2001 | Gordon |
| 6,269,142 B1 | 7/2001 | Smith |
| 6,272,230 B1 | 8/2001 | Hiraoglu |
| 6,278,115 B1 | 8/2001 | Annis |
| 6,282,260 B1 | 8/2001 | Grodzins |
| 6,292,533 B1 | 9/2001 | Swift |
| 6,301,326 B2 | 10/2001 | Bjorkholm |
| 6,301,327 B1 | 10/2001 | Martens |
| 6,304,629 B1 * | 10/2001 | Conway et al. ............... 378/68 |
| 6,317,509 B1 | 11/2001 | Simanovsky |
| 6,320,933 B1 | 11/2001 | Grodzins |
| 6,324,249 B1 | 11/2001 | Fazzio |
| 6,345,113 B1 | 2/2002 | Crawford |
| 6,347,132 B1 | 2/2002 | Annis |
| 6,356,620 B1 | 3/2002 | Rothschild |
| 6,396,899 B2 | 5/2002 | Kuwabara |
| 6,418,189 B1 | 7/2002 | Schafer |
| 6,418,194 B1 | 7/2002 | McPherson |
| 6,421,420 B1 | 7/2002 | Grodzins |
| 6,424,695 B1 | 7/2002 | Grodzins |
| 6,427,891 B1 | 8/2002 | Anderson |
| 6,429,578 B1 | 8/2002 | Danielsson |
| 6,430,255 B2 | 8/2002 | Fenkart |
| 6,431,344 B1 | 8/2002 | Emmermann |
| 6,434,219 B1 | 8/2002 | Rothschild |
| 6,435,715 B1 | 8/2002 | Betz |
| 6,438,201 B1 | 8/2002 | Mazess |
| 6,442,233 B1 | 8/2002 | Grodzins |
| 6,445,765 B1 | 9/2002 | Frank |
| 6,446,782 B1 | 9/2002 | Patrick |
| 6,448,564 B1 | 9/2002 | Johnson |
| 6,453,003 B1 | 9/2002 | Springer |
| 6,453,007 B2 | 9/2002 | Adams |
| 6,456,684 B1 | 9/2002 | Mun |
| 6,459,755 B1 | 10/2002 | Li |
| 6,459,761 B1 | 10/2002 | Grodzins |
| 6,459,764 B1 | 10/2002 | Chalmers |
| 6,473,487 B1 | 10/2002 | Le |
| RE37,899 E | 11/2002 | Grodzins |
| 6,483,894 B2 | 11/2002 | Hartick |
| 6,507,025 B1 | 1/2003 | Verbinski |
| 6,528,787 B2 | 3/2003 | Katagami |
| 6,532,276 B1 | 3/2003 | Hartick |
| 6,542,574 B2 | 4/2003 | Grodzins |
| 6,542,578 B2 | 4/2003 | Ries |
| 6,542,580 B1 | 4/2003 | Carver |
| 6,543,599 B2 | 4/2003 | Jasinetzky |
| 6,546,072 B1 | 4/2003 | Chalmers |
| 6,552,346 B2 | 4/2003 | Verbinski |
| 6,556,653 B2 | 4/2003 | Hussein |
| 6,563,903 B2 | 5/2003 | Kang |
| 6,563,906 B2 | 5/2003 | Hussein |
| 6,567,496 B1 | 5/2003 | Sychev |
| 6,580,778 B2 | 6/2003 | Meder |
| 6,584,170 B2 | 6/2003 | Aust |
| 6,590,956 B2 | 7/2003 | Fenkart |
| 6,591,130 B2 | 7/2003 | Shahidi |
| 6,597,760 B2 | 7/2003 | Beneke |
| 6,606,516 B2 | 8/2003 | Levine |
| 6,618,466 B1 | 9/2003 | Ning |
| 6,621,888 B2 | 9/2003 | Grodzins |
| 6,629,593 B2 | 10/2003 | Zeitler |
| 6,636,581 B2 | 10/2003 | Sorenson |
| 6,636,623 B2 | 10/2003 | Nelson |
| 6,647,091 B2 | 11/2003 | Fenkart |
| 6,647,094 B2 | 11/2003 | Harding |
| 6,647,095 B2 | 11/2003 | Hsieh |
| 6,653,588 B1 | 11/2003 | Gillard-Hickman |
| 6,658,087 B2 | 12/2003 | Chalmers |
| 6,661,867 B2 | 12/2003 | Mario |

(56) References Cited

U.S. PATENT DOCUMENTS

| | | |
|---|---|---|
| 6,661,876 B2 | 12/2003 | Turner |
| 6,663,280 B2 | 12/2003 | Doenges |
| 6,665,373 B1 | 12/2003 | Kotowski |
| 6,665,433 B2 | 12/2003 | Roder |
| 6,687,333 B2 | 2/2004 | Carroll |
| 6,690,766 B2 | 2/2004 | Kresse |
| 6,705,357 B2 | 3/2004 | Jeon |
| 6,707,879 B2 | 3/2004 | McClelland |
| 6,713,773 B1 | 3/2004 | Lyons |
| 6,715,533 B2 | 4/2004 | Kresse |
| 6,721,387 B1 | 4/2004 | Naidu |
| 6,721,391 B2 | 4/2004 | McClelland |
| 6,727,506 B2 | 4/2004 | Mallette |
| 6,735,271 B1 | 5/2004 | Rand |
| 6,737,652 B2 | 5/2004 | Lanza |
| 6,744,845 B2 | 6/2004 | Harding |
| 6,748,043 B1 | 6/2004 | Dobbs |
| 6,754,298 B2 | 6/2004 | Fessler |
| 6,760,407 B2 | 7/2004 | Price |
| 6,763,083 B2 | 7/2004 | Fernandez |
| 6,763,635 B1 | 7/2004 | Lowman |
| 6,770,884 B2 | 8/2004 | Bryman |
| 6,775,348 B2 | 8/2004 | Hoffman |
| 6,785,357 B2 | 8/2004 | Bernardi |
| 6,788,761 B2 | 9/2004 | Bijjani |
| 6,812,426 B1 | 11/2004 | Kotowski |
| 6,813,374 B1 | 11/2004 | Karimi |
| 6,816,571 B2 | 11/2004 | Bijjani |
| 6,827,265 B2 | 12/2004 | Knowles |
| 6,829,585 B1 | 12/2004 | Grewal |
| 6,830,185 B2 | 12/2004 | Tsikos |
| 6,837,422 B1 | 1/2005 | Meder |
| 6,837,432 B2 | 1/2005 | Tsikos |
| 6,839,134 B2 | 1/2005 | Saito |
| 6,839,403 B1 | 1/2005 | Kotowski |
| 6,843,599 B2 | 1/2005 | Le |
| 6,856,344 B2 | 2/2005 | Frantz |
| 6,856,667 B2 | 2/2005 | Ellengogen |
| 6,859,514 B2 | 2/2005 | Hoffman |
| 6,869,217 B2 | 3/2005 | Rasche |
| 6,876,719 B2 | 4/2005 | Ozaki |
| 6,876,724 B2 | 4/2005 | Zhou |
| 6,879,657 B2 | 4/2005 | Hoffman |
| 6,899,540 B1 | 5/2005 | Neiderman |
| 6,901,135 B2 | 5/2005 | Fox |
| 6,901,346 B2 | 5/2005 | Tracy |
| 6,906,329 B2 | 6/2005 | Bryman |
| 6,907,101 B2 | 6/2005 | Hoffman |
| 6,920,197 B2 | 7/2005 | Kang |
| 6,922,455 B2 | 7/2005 | Jurczyk |
| 6,922,460 B2 | 7/2005 | Skatter |
| 6,922,461 B2 | 7/2005 | Kang |
| 6,928,141 B2 | 8/2005 | Carver |
| 6,933,504 B2 | 8/2005 | Hoffman |
| 6,934,354 B2 | 8/2005 | Hoffman |
| 6,937,692 B2 | 8/2005 | Johnson |
| 6,940,071 B2 | 9/2005 | Ramsden |
| 6,944,264 B2 | 9/2005 | Bijjani |
| 6,947,517 B2 | 9/2005 | Hoffman |
| 6,950,492 B2 | 9/2005 | Besson |
| 6,950,493 B2 | 9/2005 | Besson |
| 6,952,163 B2 | 10/2005 | Huey |
| 6,953,935 B1 | 10/2005 | Hoffman |
| 6,957,913 B2 | 10/2005 | Renkart |
| 6,962,289 B2 | 11/2005 | Vatan |
| 6,965,314 B2 | 11/2005 | Bohinc |
| 6,968,030 B2 | 11/2005 | Hoffman |
| 6,968,034 B2 | 11/2005 | Ellengogen |
| 6,971,577 B2 | 12/2005 | Tsikos |
| 6,972,693 B2 | 12/2005 | Brown |
| 6,973,158 B2 | 12/2005 | Besson |
| 6,975,698 B2 | 12/2005 | Katcha |
| 6,978,936 B2 | 12/2005 | Tsikos |
| 6,980,627 B2 | 12/2005 | Qiu |
| 6,983,704 B1 * | 1/2006 | Ness ............... 108/55.3 |
| 6,990,171 B2 | 1/2006 | Toth |
| 6,990,172 B2 | 1/2006 | Toth |
| 6,991,371 B2 | 1/2006 | Georgeson |
| 6,993,115 B2 | 1/2006 | McGuire |
| 6,996,209 B2 | 2/2006 | Marek |
| 7,010,083 B2 | 3/2006 | Hoffman |
| 7,010,094 B2 | 3/2006 | Grodzins |
| 7,016,459 B2 | 3/2006 | Ellenbogen |
| 7,020,241 B2 | 3/2006 | Beneke |
| 7,020,242 B2 | 3/2006 | Ellenbogen |
| 7,023,956 B2 | 4/2006 | Heaton |
| 7,023,957 B2 | 4/2006 | Bijjani |
| 7,027,553 B2 | 4/2006 | Dunham |
| 7,027,554 B2 | 4/2006 | Gaultier |
| 7,028,442 B2 | 4/2006 | Merrifield |
| 7,031,430 B2 | 4/2006 | Kaucic |
| 7,031,434 B1 | 4/2006 | Saunders |
| 7,034,313 B2 | 4/2006 | Hoffman |
| 7,039,154 B1 | 5/2006 | Ellenbogen |
| 7,039,159 B2 | 5/2006 | Muenchau |
| 7,042,975 B2 | 5/2006 | Heuscher |
| 7,045,787 B1 | 5/2006 | Verbinski |
| 7,045,788 B2 | 5/2006 | Iwatschenko-Borho |
| 7,046,756 B2 | 5/2006 | Hoffman |
| 7,046,761 B2 | 5/2006 | Ellenbogen |
| 7,046,768 B1 | 5/2006 | Gilevich |
| 7,050,536 B1 | 5/2006 | Fenkart |
| 7,050,541 B2 | 5/2006 | Bittl |
| 7,054,408 B2 | 5/2006 | Jiang |
| 7,062,009 B2 | 6/2006 | Karimi |
| 7,062,011 B1 | 6/2006 | Tybinkowski |
| 7,062,074 B1 | 6/2006 | Beneke |
| 7,064,334 B2 | 6/2006 | Hoffman |
| 7,065,175 B2 | 6/2006 | Green |
| 7,065,179 B2 | 6/2006 | Block |
| 7,068,749 B2 | 6/2006 | Kollegal |
| 7,068,750 B2 | 6/2006 | Toth |
| 7,068,751 B2 | 6/2006 | Toth |
| 7,072,434 B1 | 7/2006 | Tybinkowski |
| 7,076,029 B2 | 7/2006 | Toth |
| 7,078,699 B2 | 7/2006 | Seppi |
| 7,081,628 B2 | 7/2006 | Granfors |
| 7,084,404 B2 | 8/2006 | Hoffman |
| 7,087,902 B2 | 8/2006 | Wang |
| 7,088,799 B2 | 8/2006 | Hoffman |
| 7,090,133 B2 | 8/2006 | Zhu |
| 7,092,481 B2 | 8/2006 | Hoffman |
| 7,092,485 B2 | 8/2006 | Kravis |
| 7,099,434 B2 | 8/2006 | Adams |
| 7,099,435 B2 | 8/2006 | Heumann |
| 7,103,137 B2 | 9/2006 | Seppi |
| 7,110,488 B2 | 9/2006 | Katcha |
| 7,112,797 B2 | 9/2006 | Hoge |
| 7,116,235 B2 | 10/2006 | Alioto |
| 7,116,749 B2 | 10/2006 | Besson |
| 7,116,751 B2 | 10/2006 | Ellenbogen |
| 7,119,553 B2 | 10/2006 | Yang |
| 7,123,681 B2 | 10/2006 | Ellenbogen |
| 7,127,027 B2 | 10/2006 | Hoffman |
| 7,130,374 B1 | 10/2006 | Jacobs |
| RE39,396 E | 11/2006 | Swift |
| 7,133,491 B2 | 11/2006 | Bernardi |
| 7,136,450 B2 | 11/2006 | Ying |
| 7,136,451 B2 | 11/2006 | Naidu |
| 7,139,367 B1 | 11/2006 | Le |
| 7,139,406 B2 | 11/2006 | McClelland |
| 7,142,208 B2 | 11/2006 | Lorenz |
| 7,142,629 B2 | 11/2006 | Edic |
| 7,149,278 B2 | 12/2006 | Arenson |
| 7,149,339 B2 | 12/2006 | Veneruso |
| 7,154,989 B2 | 12/2006 | Ueno |
| 7,155,812 B1 | 1/2007 | Peterson |
| 7,158,611 B2 | 1/2007 | Heismann |
| 7,162,005 B2 | 1/2007 | Bjorkholm |
| 7,162,285 B2 | 1/2007 | Owens |
| 7,164,747 B2 | 1/2007 | Ellenbogen |
| 7,164,750 B2 | 1/2007 | Nabors |
| 7,166,458 B2 | 1/2007 | Ballerstadt |
| 7,166,844 B1 | 1/2007 | Gormley |

(56) References Cited

U.S. PATENT DOCUMENTS

| | | |
|---|---|---|
| 7,167,539 B1 | 1/2007 | Hoffman |
| 7,173,998 B2 | 2/2007 | Hoffman |
| 7,177,387 B2 | 2/2007 | Yasunaga |
| 7,177,391 B2 | 2/2007 | Chapin |
| 7,187,756 B2 | 3/2007 | Gohno |
| 7,190,757 B2 | 3/2007 | Ying |
| 7,192,031 B2 | 3/2007 | Dunham |
| 7,197,113 B1 | 3/2007 | Katcha |
| 7,197,172 B1 | 3/2007 | Naidu |
| 7,203,276 B2 | 4/2007 | Arsenault |
| 7,203,629 B2 | 4/2007 | Oezis |
| 7,204,125 B2 | 4/2007 | Fine |
| 7,206,379 B2 | 4/2007 | Lemaitre |
| 7,207,713 B2 | 4/2007 | Lowman |
| 7,212,113 B2 | 5/2007 | Zanovitch |
| 7,215,731 B1 | 5/2007 | Basu |
| 7,215,737 B2 | 5/2007 | Li |
| 7,215,738 B2 | 5/2007 | Muenchau |
| 7,218,700 B2 | 5/2007 | Huber |
| 7,218,704 B1 | 5/2007 | Adams |
| 7,224,763 B2 | 5/2007 | Naidu |
| 7,224,765 B2 | 5/2007 | Ellenbogen |
| 7,224,766 B2 | 5/2007 | Jiang |
| 7,224,769 B2 | 5/2007 | Turner |
| 7,233,640 B2 | 6/2007 | Ikhlef |
| 7,236,564 B2 | 6/2007 | Hopkins |
| 7,238,945 B2 | 7/2007 | Hoffman |
| 7,238,951 B2 | 7/2007 | Disdier |
| 7,244,947 B2 | 7/2007 | Polichar |
| 7,247,856 B2 | 7/2007 | Hoge |
| 7,250,940 B2 | 7/2007 | Jayanetti |
| 7,251,310 B2 | 7/2007 | Smith |
| 7,257,189 B2 | 8/2007 | Modica et al. |
| 7,260,170 B2 | 8/2007 | Arenson |
| 7,260,171 B1 | 8/2007 | Arenson |
| 7,260,172 B2 | 8/2007 | Arenson |
| 7,260,173 B2 | 8/2007 | Wakayama |
| 7,260,174 B2 | 8/2007 | Hoffman |
| 7,260,182 B2 | 8/2007 | Toth |
| 7,260,255 B2 | 8/2007 | Polichar |
| 7,263,160 B2 | 8/2007 | Schlomka |
| 7,266,180 B1 | 9/2007 | Saunders |
| 7,272,208 B2 | 9/2007 | Yatsenko |
| 7,272,429 B2 | 9/2007 | Walker |
| 7,274,767 B2 | 9/2007 | Clayton |
| 7,277,577 B2 | 10/2007 | Ying |
| 7,279,120 B2 | 10/2007 | Cheng |
| 7,280,631 B2 | 10/2007 | De Man et al. |
| 7,282,727 B2 | 10/2007 | Retsky |
| 7,283,604 B2 | 10/2007 | De Man et al. |
| 7,283,609 B2 | 10/2007 | Possin |
| 7,295,019 B2 | 11/2007 | Yang |
| 7,295,651 B2 | 11/2007 | Delgado |
| 7,298,812 B2 | 11/2007 | Tkaczyk |
| 7,302,083 B2 | 11/2007 | Larson |
| 7,308,073 B2 | 12/2007 | Tkaczyk |
| 7,308,074 B2 | 12/2007 | Jiang |
| 7,308,076 B2 | 12/2007 | Studer |
| 7,308,077 B2 | 12/2007 | Bijjani |
| 7,317,195 B2 | 1/2008 | Eikman |
| 7,317,259 B2 | 1/2008 | Yamauchi |
| 7,317,390 B2 | 1/2008 | Huey |
| 7,319,737 B2 | 1/2008 | Singh |
| 7,322,745 B2 | 1/2008 | Agrawal |
| 7,324,625 B2 | 1/2008 | Eilbert |
| 7,327,853 B2 | 2/2008 | Ying |
| 7,330,527 B2 | 2/2008 | Hoffman |
| 7,330,535 B2 | 2/2008 | Arenson |
| 7,333,587 B2 | 2/2008 | De Man et al. |
| 7,333,588 B2 | 2/2008 | Mistretta |
| 7,333,589 B2 | 2/2008 | Ellenbogen |
| 7,335,887 B1 | 2/2008 | Verbinski |
| 7,336,769 B2 | 2/2008 | Arenson |
| 7,349,525 B2 | 3/2008 | Morton |
| 7,352,843 B2 | 4/2008 | Hu |
| 7,356,174 B2 | 4/2008 | Leue |
| 7,369,463 B1 | 5/2008 | Van Dullemen |
| 7,369,640 B2 | 5/2008 | Seppi |
| 7,369,643 B2 | 5/2008 | Kotowski |
| 7,372,040 B2 | 5/2008 | Polichar |
| 7,372,944 B2 | 5/2008 | Bernhardt |
| 7,379,530 B2 | 5/2008 | Hoff |
| 7,386,092 B2 | 6/2008 | Kang |
| 7,397,891 B2 | 7/2008 | Johnson |
| 7,400,701 B1 | 7/2008 | Cason |
| 7,420,174 B2 | 9/2008 | Kurita |
| 7,429,738 B2 | 9/2008 | Li |
| 7,440,543 B2 | 10/2008 | Morton |
| 7,453,987 B1 | 11/2008 | Richardson |
| 7,460,639 B2 | 12/2008 | Tudor |
| 7,470,914 B2 | 12/2008 | Li |
| 7,471,764 B2 | 12/2008 | Kaval |
| 7,475,428 B2 | 1/2009 | Smith |
| 7,475,866 B2 | 1/2009 | Hu |
| 7,483,510 B2 | 1/2009 | Carver |
| 7,483,511 B2 | 1/2009 | Bendahan |
| 7,486,768 B2 | 2/2009 | Allman |
| 7,492,855 B2 | 2/2009 | Hopkins |
| 7,500,931 B2 | 3/2009 | Rosemeier |
| 7,505,556 B2 | 3/2009 | Chalmers |
| 7,505,557 B2 | 3/2009 | Modica |
| 7,505,562 B2 | 3/2009 | Dinca |
| 7,512,215 B2 | 3/2009 | Morton |
| 7,517,149 B2 | 4/2009 | Agrawal |
| 7,519,148 B2 | 4/2009 | Kotowski |
| 7,525,101 B2 | 4/2009 | Grodzins |
| 7,526,064 B2 | 4/2009 | Akery |
| 7,538,325 B2 | 5/2009 | Mishin |
| 7,547,888 B2 | 6/2009 | Cooke |
| 7,551,714 B2 | 6/2009 | Rothschild |
| 7,551,715 B2 | 6/2009 | Rothschild |
| 7,551,718 B2 | 6/2009 | Rothschild |
| 7,555,099 B2 | 6/2009 | Rothschild |
| 7,564,939 B2 | 7/2009 | Morton |
| 7,580,505 B2 | 8/2009 | Kang |
| 7,593,506 B2 | 9/2009 | Cason |
| 7,593,510 B2 | 9/2009 | Rothschild |
| 7,649,976 B2 | 1/2010 | Georgeson |
| 7,663,109 B2 | 2/2010 | Kang |
| 7,684,538 B2 | 3/2010 | Morton |
| 7,720,195 B2 | 5/2010 | Allman |
| 7,724,869 B2 | 5/2010 | Wang |
| 7,734,066 B2 | 6/2010 | DeLia |
| 7,738,687 B2 | 6/2010 | Tortora |
| 7,741,612 B2 | 6/2010 | Clothier |
| 7,742,568 B2 | 6/2010 | Smith |
| 7,760,103 B2 | 7/2010 | Frank |
| 7,762,760 B2 | 7/2010 | Takehara |
| 7,769,133 B2 | 8/2010 | Carver |
| 7,783,003 B2 | 8/2010 | Clayton |
| 7,783,004 B2 | 8/2010 | Kotowski |
| 7,783,005 B2 | 8/2010 | Kaval |
| 7,796,734 B2 | 9/2010 | Mastronardi |
| 7,800,073 B2 | 9/2010 | Clothier |
| 7,809,104 B2 | 10/2010 | Foland |
| 7,809,109 B2 | 10/2010 | Mastronardi |
| 7,817,775 B2 | 10/2010 | Kang |
| 7,817,776 B2 | 10/2010 | Agrawal |
| 7,835,486 B2 | 11/2010 | Basu |
| 7,860,213 B2 | 12/2010 | Akery |
| 7,876,879 B2 | 1/2011 | Morton |
| 7,876,880 B2 | 1/2011 | Kotowski |
| 7,885,375 B2 | 2/2011 | Bernard De Man et al. |
| 7,903,783 B2 | 3/2011 | Modica |
| 7,952,079 B2 | 5/2011 | Neustadter |
| 7,957,506 B2 | 6/2011 | Smith |
| 7,963,695 B2 | 6/2011 | Kotowski |
| 7,965,695 B2 | 6/2011 | Valko |
| 7,973,697 B2 | 7/2011 | Reilly |
| 7,991,113 B2 | 8/2011 | Carver |
| 7,991,117 B2 | 8/2011 | Chen |
| 7,995,705 B2 | 8/2011 | Allman |
| 8,000,436 B2 | 8/2011 | Seppi |
| 8,031,903 B2 | 10/2011 | Paresi |

(56) References Cited

U.S. PATENT DOCUMENTS

| | | |
|---|---|---|
| 8,054,938 B2 | 11/2011 | Kaval |
| 8,059,781 B2 | 11/2011 | Agrawal |
| 8,148,693 B2 | 4/2012 | Ryge |
| 8,170,177 B2 | 5/2012 | Akery |
| 8,173,970 B2 | 5/2012 | Inbar |
| 8,194,822 B2 | 6/2012 | Rothschild |
| 8,263,938 B2 | 9/2012 | Bjorkholm |
| 8,275,091 B2 | 9/2012 | Morton |
| 8,350,747 B2 | 1/2013 | Delia |
| 8,356,937 B2 | 1/2013 | Kotowski |
| 8,385,501 B2 | 2/2013 | Allman |
| 8,389,941 B2 | 3/2013 | Bendahan |
| 8,389,942 B2 | 3/2013 | Morton |
| 8,401,147 B2 | 3/2013 | Ryge |
| 8,433,036 B2 | 4/2013 | Morton |
| 8,437,448 B2 | 5/2013 | Langeveld |
| 8,451,974 B2 | 5/2013 | Morton |
| 8,457,275 B2 | 6/2013 | Akery |
| 8,483,356 B2 | 7/2013 | Bendahan |
| 8,491,189 B2 | 7/2013 | Kotowski |
| 8,498,376 B2 | 7/2013 | Modica |
| 8,502,699 B2 | 8/2013 | Zerwekh |
| 8,503,605 B2 | 8/2013 | Morton |
| 8,579,506 B2 | 11/2013 | Morton |
| 8,582,720 B2 | 11/2013 | Morton |
| 8,644,453 B2 | 2/2014 | Morton |
| 8,668,386 B2 | 3/2014 | Morton |
| 8,687,765 B2 | 4/2014 | Kotowski |
| 8,735,833 B2 | 5/2014 | Morton |
| 8,744,033 B2 | 6/2014 | Oosaka |
| 8,750,452 B2 | 6/2014 | Kaval |
| 8,798,232 B2 | 8/2014 | Bendahan |
| 8,831,176 B2 | 9/2014 | Morton |
| 8,837,670 B2 | 9/2014 | Akery |
| 2002/0031202 A1 | 3/2002 | Callerame |
| 2002/0038753 A1 | 4/2002 | Ursu |
| 2002/0045152 A1 | 4/2002 | Viscardi |
| 2003/0023592 A1 | 1/2003 | Modica |
| 2003/0085163 A1 | 5/2003 | Chan |
| 2003/0185340 A1 | 10/2003 | Frantz |
| 2004/0062346 A1 | 4/2004 | Fernandez |
| 2004/0086078 A1 | 5/2004 | Adams |
| 2004/0101098 A1 | 5/2004 | Bijjani |
| 2004/0125914 A1 | 7/2004 | Kang |
| 2004/0141584 A1 | 7/2004 | Bernardi |
| 2004/0178339 A1 | 9/2004 | Gentile |
| 2004/0202287 A1* | 10/2004 | Muller .................. 378/199 |
| 2004/0213378 A1 | 10/2004 | Zhou |
| 2004/0258198 A1 | 12/2004 | Carver |
| 2004/0258305 A1 | 12/2004 | Burnham |
| 2005/0008119 A1 | 1/2005 | McClelland |
| 2005/0008120 A1 | 1/2005 | Ellenbogen |
| 2005/0023479 A1 | 2/2005 | Grodzins |
| 2005/0031076 A1 | 2/2005 | McClelland |
| 2005/0100135 A1 | 5/2005 | Lowman |
| 2005/0117683 A1 | 6/2005 | Mishin |
| 2005/0117700 A1 | 6/2005 | Peschmann |
| 2005/0156734 A1 | 7/2005 | Zerwekh |
| 2005/0169421 A1 | 8/2005 | Muenchau |
| 2005/0226364 A1 | 10/2005 | Bernard De Man |
| 2005/0251397 A1 | 11/2005 | Zanovitch |
| 2006/0056584 A1 | 3/2006 | Allman |
| 2006/0115109 A1 | 6/2006 | Whitson |
| 2006/0126772 A1 | 6/2006 | Hu |
| 2006/0140341 A1 | 6/2006 | Carver |
| 2006/0215811 A1 | 9/2006 | Modica |
| 2006/0249685 A1 | 11/2006 | Tanaka |
| 2006/0274916 A1 | 12/2006 | Chan |
| 2007/0009088 A1 | 1/2007 | Edic |
| 2007/0085010 A1 | 4/2007 | Letant |
| 2007/0087885 A1 | 4/2007 | Rosemeier |
| 2007/0110215 A1 | 5/2007 | Hu |
| 2007/0151783 A1 | 7/2007 | Yamauchi |
| 2007/0194909 A1 | 8/2007 | Garfield |
| 2007/0269005 A1 | 11/2007 | Chalmers |
| 2007/0280416 A1 | 12/2007 | Bendahan |
| 2007/0280502 A1 | 12/2007 | Paresi |
| 2008/0044801 A1 | 2/2008 | Modica |
| 2008/0056432 A1 | 3/2008 | Pack |
| 2008/0123809 A1 | 5/2008 | Tudor |
| 2008/0156992 A1 | 7/2008 | Kang |
| 2008/0198970 A1 | 8/2008 | Kirshner |
| 2008/0205594 A1 | 8/2008 | Bjorkholm |
| 2008/0211431 A1 | 9/2008 | Mishin |
| 2009/0257555 A1 | 10/2009 | Chalmers |
| 2010/0020937 A1 | 1/2010 | Hautmann |
| 2010/0177868 A1 | 7/2010 | Smith |
| 2011/0019797 A1 | 1/2011 | Morton |
| 2011/0135060 A1 | 6/2011 | Morton |
| 2011/0176660 A1 | 7/2011 | Morton |
| 2011/0216881 A1 | 9/2011 | Modica |
| 2012/0099710 A1 | 4/2012 | Kotowski |
| 2012/0134473 A1 | 5/2012 | Morton |
| 2012/0177176 A1 | 7/2012 | Carver |
| 2013/0039472 A1 | 2/2013 | Morton |

FOREIGN PATENT DOCUMENTS

| | | |
|---|---|---|
| EP | 77018 | 4/1983 |
| EP | 0077018 A1 | 4/1983 |
| EP | 0176314 | 4/1986 |
| EP | 0261984 A2 | 3/1988 |
| EP | 0287707 | 10/1988 |
| EP | 0417965 | 3/1991 |
| EP | 0432568 | 6/1991 |
| EP | 0531993 A1 | 3/1993 |
| EP | 0584871 A1 | 3/1994 |
| EP | 0864884 A2 | 9/1998 |
| EP | 0919186 A2 | 6/1999 |
| EP | 0924742 A2 | 6/1999 |
| EP | 0930046 A2 | 7/1999 |
| EP | 0963925 A2 | 12/1999 |
| EP | 1277439 A1 | 1/2003 |
| EP | 1374776 A1 | 1/2004 |
| EP | 1413898 A1 | 4/2004 |
| EP | 2255224 | 12/2010 |
| FR | 2328280 A1 | 5/1977 |
| GB | 1497396 A | 1/1978 |
| GB | 1526041 A | 9/1978 |
| GB | 2015245 A | 9/1979 |
| GB | 2089109 A | 6/1982 |
| GB | 2212903 A | 8/1989 |
| GB | 2255634 A | 11/1992 |
| GB | 2277013 A | 10/1994 |
| GB | 2337032 A | 11/1999 |
| GB | 2404431 | 2/2005 |
| GB | 2409268 A | 6/2005 |
| GB | 2424065 A | 9/2006 |
| GB | 2437777 A | 11/2007 |
| GB | 2438317 A | 11/2007 |
| GB | 2470161 | 11/2010 |
| GB | 2470163 | 11/2010 |
| GB | 2470330 | 11/2010 |
| JP | 570175247 | 10/1982 |
| JP | 59016254 | 1/1984 |
| JP | 5975549 | 4/1984 |
| JP | 600015546 | 1/1985 |
| JP | 600021440 | 2/1985 |
| JP | H10211196 A | 8/1998 |
| JP | H11230918 A | 8/1999 |
| JP | 2001176408 | 6/2001 |
| JP | 2001233440 A | 8/2001 |
| JP | 2003126075 A | 5/2003 |
| JP | 2004000605 A | 1/2004 |
| JP | 2005013768 A | 1/2005 |
| WO | 9528715 A2 | 10/1995 |
| WO | 9802763 A1 | 1/1998 |
| WO | 9803889 A1 | 1/1998 |
| WO | 9820366 A1 | 5/1998 |
| WO | 9855851 A1 | 12/1998 |
| WO | 9939189 A2 | 8/1999 |
| WO | 9960387 A2 | 11/1999 |
| WO | 0033060 A2 | 6/2000 |
| WO | 0159485 | 8/2001 |

(56) References Cited

FOREIGN PATENT DOCUMENTS

| | | |
|---|---|---|
| WO | 0159485 A1 | 8/2001 |
| WO | 03051201 A2 | 6/2003 |
| WO | 03105159 | 12/2003 |
| WO | 2004010127 A1 | 1/2004 |
| WO | 2004037088 | 5/2004 |
| WO | 2004111625 | 12/2004 |
| WO | 2005091227 | 9/2005 |
| WO | 2005098400 A2 | 10/2005 |
| WO | 2006036076 A1 | 4/2006 |
| WO | 2006045019 | 4/2006 |
| WO | 2006078691 A2 | 7/2006 |
| WO | 2006095188 | 9/2006 |
| WO | 2005084351 | 11/2006 |
| WO | 2006135586 | 12/2006 |
| WO | 2007035359 A2 | 3/2007 |
| WO | 2007051092 | 5/2007 |
| WO | 2007055720 A2 | 5/2007 |
| WO | 2007068933 A1 | 6/2007 |
| WO | 2007103216 A2 | 9/2007 |
| WO | 2008017983 A2 | 2/2008 |
| WO | 2009027667 A2 | 3/2009 |
| WO | 2009088706 | 9/2009 |
| WO | 2009106803 | 9/2009 |
| WO | 2009106815 | 9/2009 |
| WO | 2009106857 | 9/2009 |
| WO | 2009141613 | 11/2009 |
| WO | 2009141615 | 11/2009 |
| WO | 2009137698 | 12/2009 |
| WO | 2009150416 A2 | 12/2009 |
| WO | 2010135620 | 1/2011 |
| WO | 2011008718 | 1/2011 |
| WO | 2011069024 A1 | 6/2011 |
| WO | 2011087861 | 7/2011 |
| WO | 2011095810 | 8/2011 |
| WO | 2012109273 | 8/2012 |
| WO | 2012174265 | 12/2012 |

OTHER PUBLICATIONS

Notice of Allowance dated Dec. 24, 2014 for U.S. Appl. No. 13/775,256.
International Search Report for PCT/US2008/087654, date of mailing, Jul. 6, 2009, Rapiscan Security Products, Inc.
International preliminary report on patentability PCT/US2012/024184, issued on Aug 13, 2013, Rapiscan Systems Inc.
International Search Report PCT/US2012/024184, mailed on Jul. 27, 2012, Rapiscan Systems Inc.
International Search Report PCT/US2012/042493, mailed on Oct. 1, 2012, Rapiscan Systems Inc.
International Search Report PCT/GB2009/000515, Feb. 23, 2010, Rapiscan Security Products, Inc.
International Search Report for PCT/GB2009/000497, Jan. 22, 2010.
International Search Report PCT/GB2009/001444, Apr. 6, 2010, Rapiscan Security Products.
International Search Report for PCT/GB2009/000556, Feb. 19, 2010, Rapiscan Security Products, Inc.
International Search Report PCT/GB2009/001277, Jul. 20, 2010, Rapiscan Systems, Inc.
Mobile X-Ray Inspection Systems, Internet Citation, Feb. 12, 2007, pp. 1-2, URL:http://web.archive.org/web/20070212000928/http://www.bombdetecti-on.com/cat--details.php?catid=20.
Molchanov P A et al: 'Nanosecond gated optical sensors for ocean optic applications' Sensors Applications Symposium, 2006, Proceedings of the 2006 IEEE Hourston, Texas, USA Feb. 7-9, 2006, Piscataway, NJ, USA,IEEE, Feb. 7, 2006, pp. 147-150, XP010917671 ISBN: 978-0-7803-9580-0.
International Search Report for PCT/US10/58809; Rapiscan Systems Inc.; Apr. 19, 2011.
International Search Report for PCT/GB2009/001250, Mar. 2, 2010, Rapiscan Security Products Inc.
International Search Report for PCT/GB2009/001275, Jul. 24, 2009, Rapiscan Security Products Inc.
International Search Report for PCT/US10/35720, date of mailing, Nov. 15, 2010, Rapiscan Security Products, Inc.
Smith C. R. et al: 'Application of 450 kV computed tomography to engine blocks with steel liners' Materials Evaluation vol. 65, No. 5, 2007, pp. 458-461, XP055108238.
International Search Report and Written Opinion for PCT/US2010/041757, Oct. 12, 2010.
European Patent Office, International Search Report and Written Opinion of the International Searching Authority, PCT/US2005/011382, Oct. 21, 2005.
European Patent Office, International Search Report, International Application No. PCT/US99/28266, dated Sep. 6, 2000, 3 pages.
International Search Report, PCT/US2007/066936; dated: Sep. 30, 2008, 5 pages.
International Search Report, PCT/US1998/18642, dated Jul. 7, 1999, 4 pages.
International Search Report, PCT/US1999/028035, dated Sep. 15, 2000, 6 pages.
Written Opinion of the International Searching Authority, PCT/US2007/066936, dated Sep. 30, 2008, 7 pages.
International Bureau of WIPO, International Preliminary Report on Patentability, PCT/US2005/011382, dated Oct. 19, 2006, 7 pages.
Mertz, L.N., et al, "Rotational aperture synthesis for x rays", Journal. Optical Society of America, vol. 3, Dec. 1986, pp. 2167-2170.
International Preliminary Report on Patentability, PCT/US2012/024182, issued on Aug. 13, 2013, Rapiscan Systems Inc.
International Search Report, PCT/US2012/024182 mailed on Aug. 20, 2012, Rapiscan Systems Inc.
International Search Report for PCT/US2010/061908, mailed on Apr. 2, 2012, Rapiscan Systems, Inc.
International Search Report for PCT/GB2006/000859, mailed on May 19, 2006, Corus UK Ltd.
International Search Report for PCT/GB2011/050182, Dec. 28, 2011.
International Search Report for PCT/US11/21758; Jul. 7, 2011, Rapiscan Systems Inc.
Office Action dated May 13, 2015 for U.S. Appl. No. 14/601,112.
Notice of Allowance dated Jun. 11, 2015 for U.S. Appl. No. 12/919,483.
International Search Report for PCT/GB2009/000575, Apr. 7, 2010, Rapiscan Security Products Inc.
International Search Report for PCT/GB2004/001747, Aug. 10, 2004, CXR Ltd.
International Search Report for PCT/US2007/005444, Oct. 29, 2007, Telesecurity Sciences, Inc.
International Search Report for PCT/US2006/11492, Oct. 11, 2007, United Technologies Corporation.
Sun Olapiriyakul and Sanchoy Das, Design and analysis of a two-stage security screening and inspection system, Journal of Air Transport Management, vol. 13, Issue 2, Mar. 2007, pp. 67-74.
Supplementary Partial European Search Report for EP12744504, Nov. 13, 2004.
Extended European Search Report for Application No. EP20120744504, dated Jan. 14, 2015.
Office Action dated Apr. 10, 2015 for U.S. Appl. No. 14/491,825.
Office Action dated Dec. 4, 2014 for U.S. Appl. No. 13/168,440.
Office Action dated May 20, 2015 for U.S. Appl. No. 13/168,440.
Notice of Allowance dated Mar. 31, 2015 for U.S. Appl. No. 13/922,529.

* cited by examiner

X-RAY IMAGING SYSTEM HAVING IMPROVED MOBILITY

CROSS-REFERENCE TO RELATED APPLICATIONS

The present application is a continuation of U.S. patent application Ser. No. 12/848,985, which was filed on Aug. 2, 2010. U.S. patent application Ser. No. 12/848,985 is a continuation of U.S. patent application Ser. No. 12/275,386, which issued as U.S. Pat. No. 7,783,005, which is a continuation of U.S. patent application Ser. No. 11/404,386, which issued as U.S. Pat. No. 7,471,764, which relies on, for priority, U.S. Provisional Patent Application No. 60/671,900, entitled "X-Ray System Having Improved Weather Resistance", filed on Apr. 15, 2005

FIELD OF THE INVENTION

The present application generally relates to the field of radiant energy imaging systems for detecting concealed objects, and more specifically to a detection system capable of operating in rugged, intense, and/or inclement weather environments. Specifically, the present application is an X-ray inspection system having improved weather resistance. More specifically, the present application is designed for use in outdoor venues and extreme temperatures.

BACKGROUND OF THE INVENTION

The inspection of baggage and/or other cargo at transit points such as airports and shipping ports has become almost universally mandatory. Luggage or cargo can be used for illegal transportation of contraband such as explosives, weapons, narcotics and dangerous chemicals. This warrants a rapid and accurate inspection system for determining the presence of concealed illegal materials.

X-ray scanning systems are the most widely used detection systems that provide for efficient inspection without the need for opening baggage. In conventional X-ray baggage systems, X-ray beams are directed through baggage as it is moved on a conveyor belt in a horizontal direction. The X-rays that have passed through the baggage are then processed for display on a video monitor to provide images of the contents of the baggage.

In general, conventional X-ray inspection systems work well within indoor environments, such as at airports. Conventional inspection systems, however, are also employed at ports, border crossings and customs checkpoints and/or sports venues, where space for housing and structures are not readily available. Thus, the ability of a system to operate outdoors becomes an important consideration.

Several components of conventional X-ray baggage systems are readily susceptible to damage when operating in inclement environments. For example, if a baggage inspection system is deployed in maritime environments such as a naval port, it must be able to endure the rigors of rain, sleet, salt spray and salt fog during operation.

These inclement weather elements could cause structural damage to conventional radiation shielding for the X-rays, thereby rendering the system hazardous to operate. Other parts of an X-ray inspection system that can be damaged due to moisture, humidity, dust and extreme temperatures, including the X-ray tube assembly and the collimator, which may alter the emission and scattering of X-rays, and the motors. In this case, not only the imaging quality of the system is adversely affected, but it also becomes electrically unsafe and unreliable.

Although most baggage inspection systems have a shielded housing for the X-ray tube, this alone is not sufficient to ensure unhindered functioning of the system in adverse weather conditions.

Attempts at improving the functioning of X-ray detection systems have largely focused on compensating for the effects of environmental factors on the system's detection capability.

For example, U.S. Pat. No. 5,970,113 discloses a CT scanning system having a radiation source for directing radiation through a region and an array of detectors for receiving radiation from the region while scanning the region and for generating detector signals indicative of the received radiation, a method of compensating for electrical currents that are generated by the detectors independently of radiation received by the detectors, said method comprising: generating a calibration relationship for the array of detectors, said generating comprising: varying the temperature of the array of detectors, measuring the electrical currents generated by the detectors as the temperature of the detectors is varied, characterizing the variation in the electrical currents with temperature, using the variation in the electrical currents with temperature, generating a set of first detector offset signals to be applied to the detector signals generated while scanning the region; after generating the calibration relationship, sensing a first temperature of the array of detectors; measuring a first updated detector offset signal associated with the first temperature; scanning the region to generate a detector signal; sensing a second temperature of the array of detectors; using the second temperature, the calibration relationship, and the first updated detector offset signal, adjusting the first updated detector offset signal to generate an adjusted detector offset signal such that the adjusted detector offset signal is based on the first updated detector offset signal, the second temperature and the calibration relationship; and applying the adjusted detector offset signal to the detector signal.

This abovementioned prior art system, however, does not address the potential structural and internal damage that a detection system can incur when operated in harsh weather conditions. Conventional prior art baggage inspection systems are thus presently limited in their ability to withstand the effects of unfavorable and inclement operating environments.

What is therefore needed is a baggage inspection system that is capable of delivering optimum threat detection performance when operated in inclement weather.

Since dust or moisture on the baggage itself may also harm an inspection system, what is also needed is a baggage inspection system that is designed to both withstand inclement weather conditions and remain substantially unaffected by the type of baggage being scanned.

What is also needed is a system that is designed for mobility.

SUMMARY OF THE INVENTION

It is an object of the present invention to provide a radiation inspection system, such as an X-ray system, that can operate efficiently even in inclement weather conditions while being highly mobile. Thus the improved inspection system of the present invention is capable of operating in high temperature and corrosive environments and is designed to withstand moisture, dirt and/or dust from the articles of inspection as well. The X-ray system can be used to identify any type of item, including bombs, metals, knives, razors, explosives, drugs, narcotics, organic matter, such as plants, seeds, animals, insects, or meat products, or any other type of threat or undesirable item.

In accordance with an object of the present invention, one embodiment of the X-ray system comprises a conveyor belt system that loops along the external body of the x-ray system, instead of on the inside, as with conventional X-ray systems.

In another embodiment, the X-ray system of the present invention optionally comprises internal dehumidification devices and external vacuum-type cleaning devices to remove moisture and dust/dirt from the system.

In accordance with still another object of the present invention, the X-ray system comprises temperature regulating devices, such as internal cooling devices such as air conditioning and/or exhaust fans to remove heat generated during operation of the system as well as to cool the system from external high temperatures and heaters for warming the system in cold environments. The system preferably further comprises controls to either heat or cool the system.

It is also an object of the present invention to provide an inspection system that is capable of operating in outdoor weather conditions with minimal protective covering, limited, in one exemplary use, to an overhead canvas cover.

According to another aspect of the present invention, the inspection system is capable of at dual voltages (110/220 VAC) to comply with power requirements in virtually any geography.

In accordance with yet another object of the present invention the X-ray inspection system is portable and can be efficiently transported. A rugged, labeled, removable conveyor casing made up of either stainless steel or marine lumber material is provided for the system, which acts as a protective cover when the system is not in use and also when the system is to be transported from one place to another. Additional fixtures, such as fork tubes to facilitate movement using a standard forklift and sling-lift eyelet points to be hooked to the slings of a crane and be airlifted, are also provided that enable ease of transportation of the inspection system.

An embodiment of the present invention comprises software algorithms to process scan data to search the contents of an inspected object, such as baggage, for targeted material. The system differentiates low atomic number (low-Z), medium atomic number (medium-Z) and high atomic number (high-Z) materials by analyzing the size and dual energy transmissions of the object examined. The thus differentiated regions of the object are displayed to an operator in the form of a suitably color coded image.

A yet another embodiment of the present invention comprises software for training and testing the X-ray screening operators that randomly inserts fictional threat items such as guns, bombs, or knives into the X-ray image of the actual item undergoing screening.

In one embodiment, the X-ray imaging system for searching an object for concealed threats comprises an X-ray source encased in a first enclosure, a conveyor belt assembly arranged to loop around the external underside of said imaging device, an electronics system, such as a computer, detectors, data acquisition electronics, or power electronics, for controlling the X-ray source, processing data, or managing acquired images, and a conveyor belt. The electronic system is encased in at least one second enclosure. The system also includes a base frame physically integrated with at least one of said first or second enclosure wherein said base frame comprises a connector for transporting the system, and a display device for presenting an image of said object to an operator.

Optionally, the X-ray imaging system further comprises a plurality of cleaning elements for removing contaminants from said conveyor belt, wherein said cleaning element is at least one of a brush, blower, cleaning pad, or ionizer. The X-ray imaging system further comprises a plurality of heating elements for heating at least one of said X-ray source and electronics system. The X-ray imaging system further comprises a sensor for sensing a temperature and a controller wherein said controller controls the activation of said X-ray source or said electronics and wherein said controller activates said X-ray source or said electronics when said temperature sensed by said sensor exceeds a predetermined temperature. Optionally, the connector comprises at least one of a tube, beam, hook, indentation, or metal projection.

In one embodiment, the X-ray imaging system for searching an object for concealed threats comprises an X-ray source encased in a first enclosure, a conveyor belt assembly arranged to loop through the imaging device, an electronics system for controlling the X-ray source and conveyor belt, wherein said electronic system is encased in a plurality of separate enclosures, a base frame physically integrated with at least one of said first or plurality of separate enclosures wherein said base frame comprises a connector for transporting the system, and a display device for presenting an image of said object to an operator.

Optionally, the X-ray imaging system further comprises a plurality of cleaning elements for removing contaminants from said conveyor belt, wherein said cleaning element is at least one of a brush, blower, cleaning pad, or ionizer. The X-ray imaging system further comprises a plurality of heating elements for heating at least one of said X-ray source and electronics system. The X-ray imaging system further comprises a sensor for sensing a temperature and a controller wherein said controller controls the activation of said X-ray source or said electronics and wherein said controller activates said X-ray source or said electronics when said temperature sensed by said sensor exceeds a predetermined temperature. Optionally, the connector comprises at least one of a tube, beam, hook, indentation, or metal projection. Optionally, the X-ray imaging system further comprises removable covers enclosing at least a portion of said conveyor belt.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

The methods and systems described herein are directed towards finding, locating, and confirming threat items and substances. The present invention is specifically directed towards an improved inspection system for screening objects at security locations. The system of the present invention is capable of functioning in inclement weather and rugged operating environments while retaining the efficiency of the screening process.

More specifically, the present invention is directed towards an x-ray system for use in adverse, outdoor weather conditions, with temperatures ranging between 0 to 110° F. (−17 to +43° C.) and is intended to be operated with minimal protective covering, such as, in one exemplary use, to an overhead canvas cover. The cover is used to provide protection from direct sunlight to the operator's eyes, and to provide an antiglare environment to control unnecessary fatigue.

The system of the present invention further comprises a conveyor belt that runs along the outside of the x-ray system, compared with conventional X-ray systems, in which the conveyor system runs through the inside of the system. This configuration helps keep moisture, dirt, dust, and other foreign elements from the bags out of the system and enables better sealing and protection of the electronics. In another embodiment, the conveyor belt entirely runs through the x-ray system with cleaning elements positioned inside the x-ray system to keep the system substantially clean.

To facilitate rapid deployment, the system is equipped with dual voltage capability (110/220 VAC) to comply with power requirements in virtually any geographical environment.

Although the embodiments are described in the context of a baggage inspection system, it should be evident to persons of ordinary skill in the art that items other than luggage such as other packages, mail, and cargo-containers, or even processed food stuffs, can also be analyzed and screened or graded and that the descriptions are exemplary and are not restrictive of the invention.

Although one preferred embodiment of the present invention is described with reference to X-ray scanning, one of ordinary skill in the art would appreciate that object screening may be performed using any available radiation imaging technique such as, but not limited to X-ray scattering, infrared imaging, milliwave imaging, RF imaging, radar imaging, holographic imaging, CT imaging, and MRI. Any imaging system that has the potential for displaying object detail may be employed.

Reference will now be made in detail to specific embodiments of the invention. While the invention will be described in conjunction with specific embodiments, it is not intended to limit the invention to one embodiment.

Figure 1:
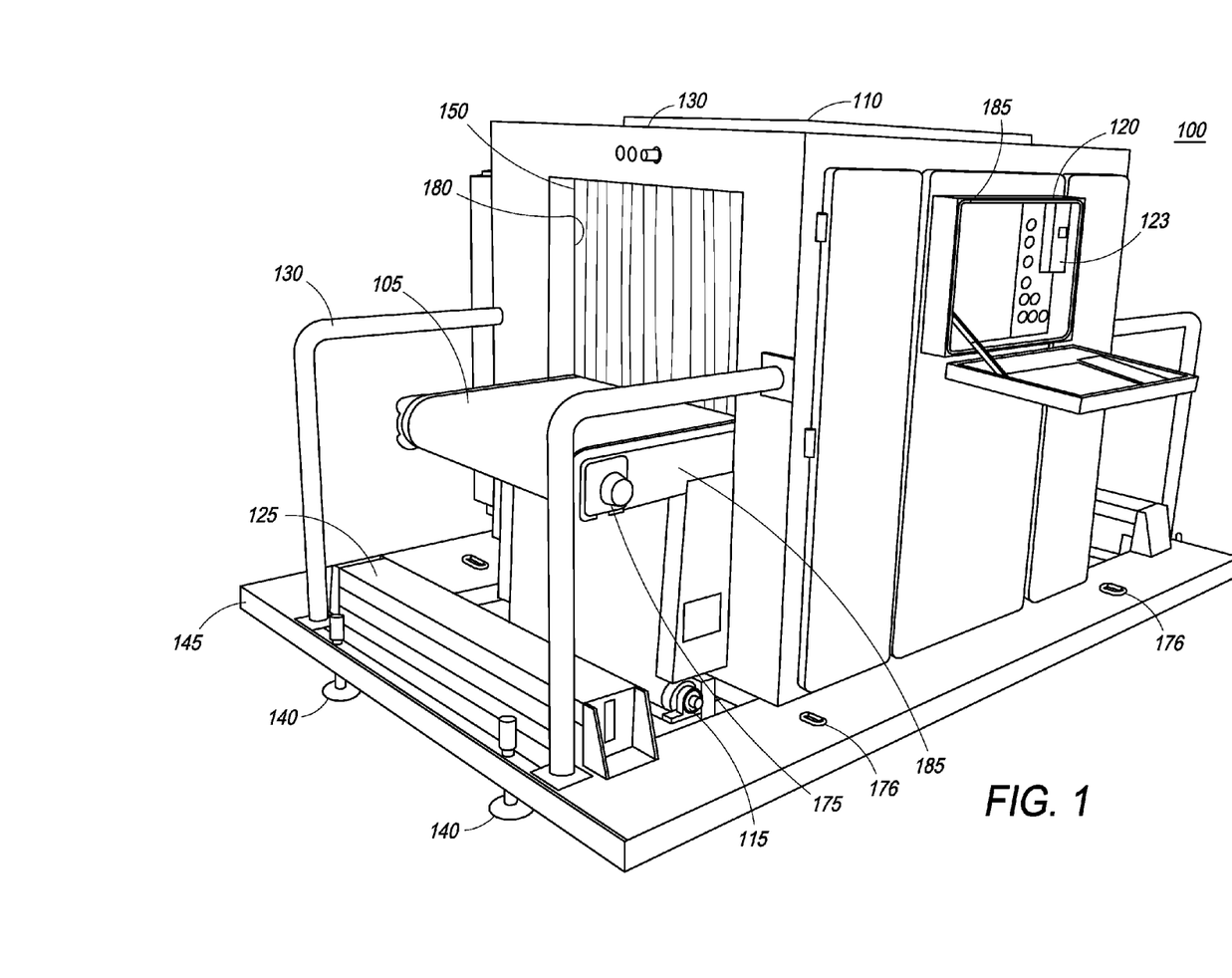
FIG. 1 illustrates the basic structural design of the X-ray imaging system having improved weather resistance of the present invention.

FIG. 1 illustrates the basic structural design of the X-ray imaging system having improved weather resistance of the present invention. Referring to FIG. 1, X-ray baggage scanning system 100 comprises an enclosure 110 mounted on a base frame 145. To provide structural reinforcement and a means by which the X-ray imaging system can be safely and reliably moved, the X-ray imaging system further comprises beams 130 that connect the enclosure 110 to the base frame 145 and base beams 125 that extend a substantial portion of the length of the base frame 145. In one embodiment, the base beams 125 are scissor lifts that can be deployed to lower wheels, thereby enabling the system to be rolled. Preferably, if the system is to remain stationary, the wheels are retracted and jacking feet 140 are used to stabilize the system.

It should be appreciated by one of ordinary skill in the art that the base frame 145 can be solid or comprised of a plurality of connected panels. The beams 130 can be L-shaped as depicted in FIG. 1, straight, or any other configuration that provides sufficient structural support. It should be appreciated that the beams 130 are positioned to protect the belt and conveyor belt from being damaged which could occur, for example, if the system is rolled against a wall or protrusion. Further the base frame 145 comprises connection points 176 that can be used to connect to hooks, cabling, or other towing mechanisms for airlifting, pushing, pulling, or otherwise moving the system 100. The connection points can comprise a hook, indentation, such as a slot cut, hole, or key slot, or any type of projection of any material type, such as metal or plastic.

The enclosure 110, base frame 145, beams 130, and base beams 125 are preferably constructed using regular steel painted with marine grade paint or stainless steel, enabling the system to function in both outdoor as well as industrial environments. In such conditions, apart from the weather elements, the system may also be exposed to caustic chemicals. This is particularly the case with industrial environments such as the packaged food or meat industry, where the X-ray scanning system may be employed for checking food materials for contaminants. In addition, any electronics, instrumentation, and display panels, such as control panel 123, are encased in regular steel painted with marine grade paint or non-corrosive stainless steel paneling 120.

The X-ray baggage scanning system 100 comprises an inspection entrance 150 covered by a lead curtain 180. Objects to be inspected are placed on an extended roller surface 185 covered by a conveyor belt 105 which extends below the extended roller surface 185, downward 175, and over base roller 115. During operation, the conveyor belt 105 moves forward, through entrance 150 and lead curtain 180, and loops around extended roller surface [not shown], downward, and over a base roller [not shown]. The conveyor belt 105 moves over the base roller 115, upward, and over extended roller surface 185. It should be appreciated that the conveyor belt 105 can move in either direction.

The conveyor apparatus of the scanning system is in constant and continual contact with different types of items under inspection, including baggage. Not all items of inspection, however, are clean, dry and/or ready to be placed into an X-ray system. This is especially true if the inspection system is operated outdoor, and in particular with inclement weather, or in rugged industrial environments. Thus, depending upon the location of inspection, the objects of inspection may be dusty, moist, or even contaminated with other environmental factors.

In one embodiment the enclosure 110, toward the base of the structure, comprises a plurality of cleaning elements [not shown] that remove water, dirt, chemicals, and other foreign substances from the conveyor belt 105 surface in order to prevent the introduction of any substances which could damage the internal detector systems and radiation sources. The cleaning elements can comprise any one of brushes, pads, blowers, dryers, ionizers, or other devices that can substantially remove foreign substances from the conveyor belt surface.

Figure 3:
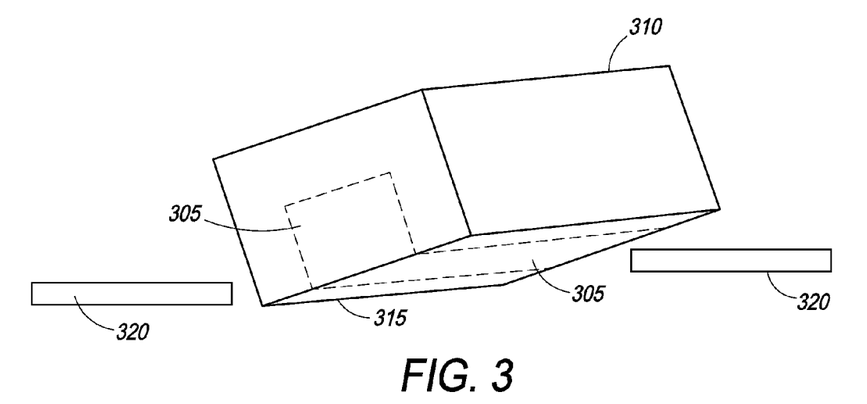
FIG. 3 is schematic of the X-ray scanning system of the present invention illustrating the external underside of the scanning system.

FIG. 3 is a block diagram of the X-ray scanning system of the present invention, in particular, illustrating the external underside of the scanning system. FIG. 3 depicts X-ray scanning system 310 further illustrating the external underside 315 of X-ray unit 310. The conveyor belt 305 is depicted with a dotted outline. If baggage placed on the conveyor 305 is wet or dirty, the external face of the belt runs on the outside of the machine to allow it to drip off, and the conveyor belt 305 is substantially dry when it comes in contact with and loops back through the X-ray unit 310. The system may further comprise at least one vacuum or suction-type cleaning device 320, which are well-known to persons of ordinary skill in the art. Vacuum or suction-type cleaning devices 320 may thus be employed to draw out the dust on the conveyor belt 305 as it runs along the outside 315 of the enclosure 310.

One of ordinary skill in the art would appreciate that the enclosure 110 encompasses a plurality of detectors and radiation sources [not shown] that expose objects to be inspected to radiation and measures the resulting output. Such detector/radiation source combinations can include X-ray transmission and/or scatter detection systems.

Figure 2:
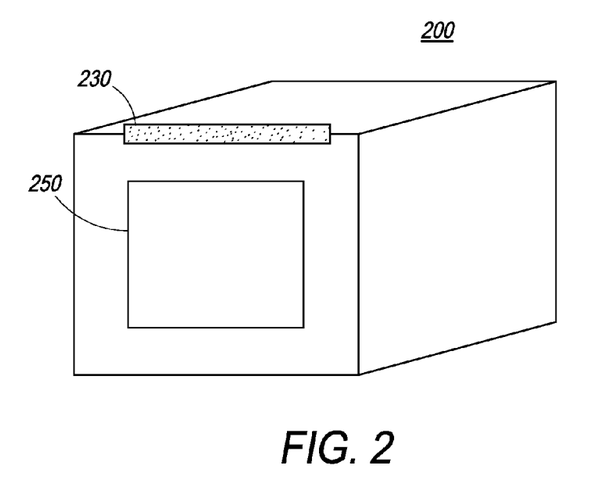
FIG. 2 is a schematic diagram illustrating the placement of an environmental control system.

Referring to FIG. 2, the system contains an environmental control system 230 that ensures the electronic components remain dry and cool. In one embodiment, the environmental control system 230 comprises an internal high-reliability, interlocked dehumidifier to ensure that the electronic components remain dry and cool. In another embodiment, the environmental control system 230 comprises an internal cooling device that compensates for the external heat as well as for the heat generated during operation. Optionally, a temperature control device or air conditioning device, known to persons of ordinary skill in the art, is interlocked internally within the system of the present invention. The air conditioning device has sufficient cooling capacity depending upon the load/size of the inspection system and the external temperatures. In another embodiment exhaust fans are provided on the chassis of the inspection system that constantly withdraw heat generated in the internal components of the machine.

In another embodiment, heaters are provided and configured to keep varied portions of the system warm. Separate heaters are preferably provided for the X-ray source and electronics. Also preferably, the electronics and X-ray source do not turn on until a threshold temperature is reached. Therefore, the system further comprises a sensor for measuring the temperature and a controller for permitting the X-ray source and/or electronics to turn on, upon reaching a predetermined threshold temperature, as determined by the sensor, and receiving an activation signal from an operator.

Figure 4:
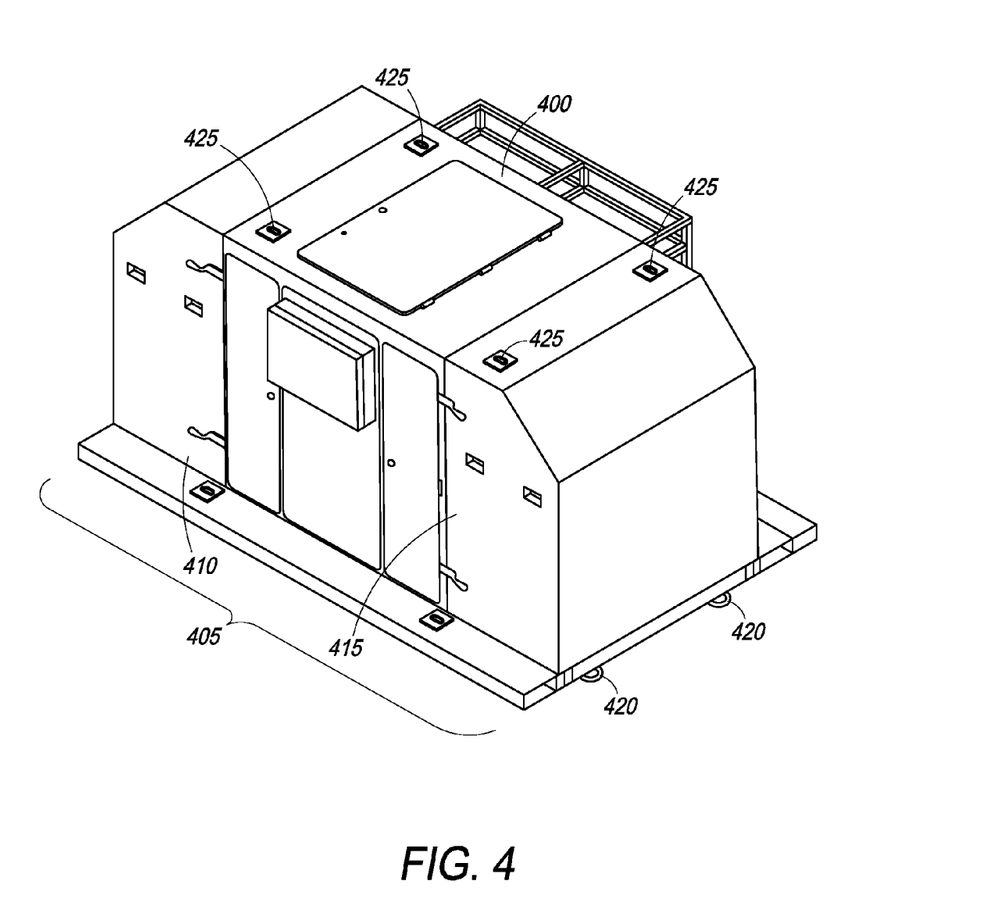
FIG. 4 depicts another embodiment of the system of present invention.

In another embodiment, a rugged, labeled, removable casing made up of either stainless steel or regular steel painted with marine grade paint is provided for the system, which acts as a protective cover for the conveyor belt when the system is not in use and also when the system is to be transported from one place to another. FIG. 4 depicts the system 400 of the present invention with the protective casing 405. The protective casing 405 is especially useful during transportation of the system 400, as it prevents damage to the belts and tunnels of the units at the time of loading and unloading. In order to enhance the ease of transportation, the protective case 405 is designed such that it fits over the system 400 in two pieces, 410 and 415, in a manner that exposes a set of fork tubes 420, which are provided to facilitate movement using a standard forklift. In addition or alternatively, threaded, sling-lift eyelet points 425 are provided at the four corners of the casing 405, which enable the system 400 to be hooked to the slings of a crane and be airlifted. Preferably, however, connection points on the base frame are used to connect to hooks, cabling, or other towing mechanisms for airlifting, pushing, pulling, or otherwise moving the system. The connection points can comprise a hook, indentation, such as a slot cut, hole, or key slot, or any type of projection of any material type, such as metal or plastic. It should be appreciated that the present configuration is designed to protect the system from damage during transport while still enabling a fast setup of the system. This is achieved by providing casing covers for only the conveyor belt and not encompassing the entire system in a separate casing or crate during transport.

In one embodiment, the system depicted in FIG. 4 has a length of 90 to 120 inches, a height of 40 to 70 inches, and a width of 50 to 80 inches. The conveyor belt, which is covered by case 405, progresses through a tunnel of dimensions 29.53 inches to 21.65 inches at a rate of 30 to 50 ft/min. The conveyor is preferably capable of handling a load of 350 to 450 lbs. The approximate weight of the system is 4000 to 4500 lbs. For power, the system has dual voltage capability (110/220 VAC). The X-ray image performance has a minimum penetration of 25 mm and a standard penetration of 29 mm. The X-ray generator is cooled using a sealed oil bath with forced air and has an anode voltage rated at 160 KV and operating at 140 KV. The X-ray generator is oriented vertically upward, toward the top-level conveyor belt. It can be stored in temperatures ranging from negative 20 degrees C. to 50 degrees C., operated in temperatures ranging from negative 17 degrees C. to 43 degrees C., and stored or operated in relative humidity ranging from 0 to 100% condensing. The system preferably complies with US military salt spray requirements embodied in MIL-STD-810F, which is incorporated herein by reference.

During operation, an item under inspection is first carried along the conveyor belt 105, which, in turn, carries the item into the aperture defining the entrance 150 to scanning system 100 and through the lead curtain 180. As the item under inspection passes through the X-scanning system 100, an image of the contents of the item is displayed upon display screen 185. The generation of X-ray transmission or scatter images is known to persons of ordinary skill in the art and will not be repeated herein.

Apart from robustness, the present invention focuses on ease of operation while maintaining high levels of performance. A preferred embodiment of the system uses preset software algorithms, as known to persons of ordinary skill in the art, to search baggage contents for targeted material. During the analysis process the size and atomic number of the material(s) are examined, and low atomic number (low-Z), medium atomic number (medium-Z) and high atomic number (high-Z) material are differentiated. This differentiation is presented to the screening operator in an easy visual manner, such as by highlighting materials with different atomic numbers in different colors. The present application incorporates the X-ray analytical systems disclosed in U.S. patent application Ser. No. 10/910,250, entitled "Automatic Alarm Resolution for Explosive Detection System", by reference.

For example, the system is capable of distinguishing between materials according to their inherent characteristics (densities) and then classifies for the operator by color. For example, but not limited to such color scheme, orange is used for low atomic density, green for medium atomic density and blue for high atomic density material. Most explosives are in the low atomic density and thus will be displayed in orange. Other low density materials such as plastics, clothing, and paper will also be shown in orange. Medium density materials such as aluminum will be displayed in green, while very dense materials like metals will be shown in blue. In situations where X-rays cannot penetrate an object due to a combination of thickness and/or density, the image color will be black. This is the case for items such as lead glass vases, and thick metals. Obviously because X-rays are not getting through a black colored item, the bag needs to be opened and inspected, as there is a concealment zone in there.

Figure 5:
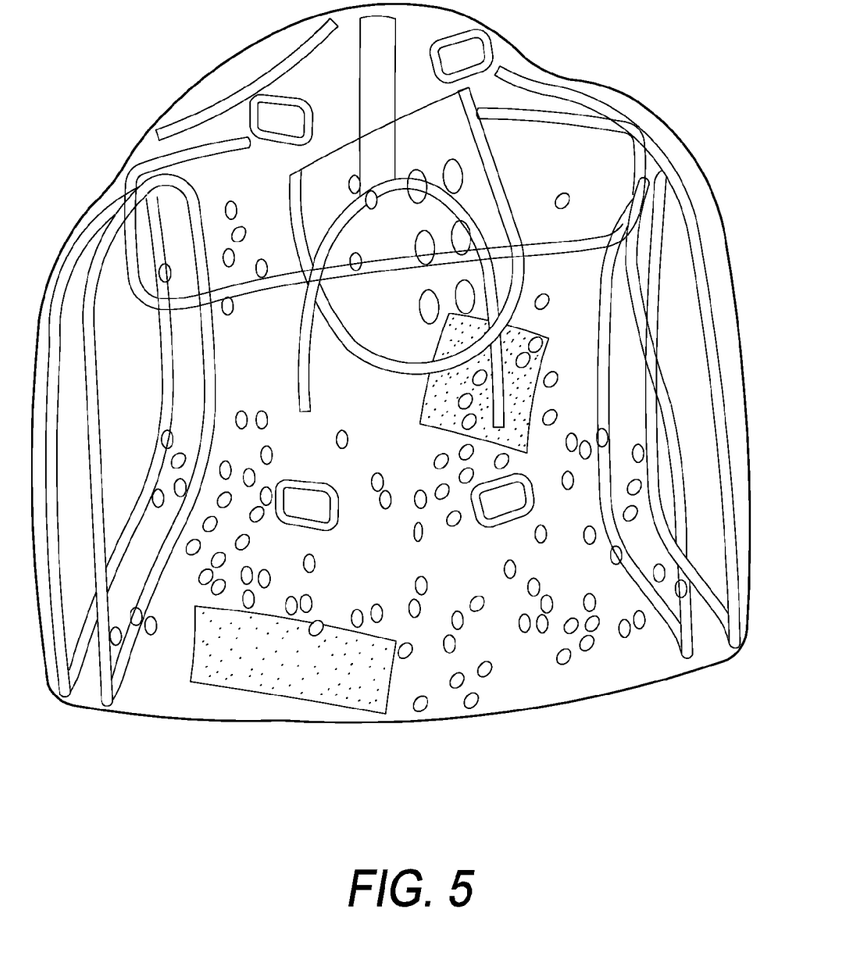
FIG. 5 illustrates an exemplary X-ray scan image with embedded fictional threat items.

Another embodiment of the system also provides a reliable and sophisticated method for the training and testing of X-ray screening personnel. This involves using a software package that randomly inserts fictional threat items such as guns, bombs, or knives into the X-ray image of the actual item undergoing screening. An example of such an image with illusory threat objects is illustrated in FIG. 5. This process enhances the alertness and threat recognition skills of the operators, and also provides performance data to supervisors for monitoring the operators' response. This application is detailed in U.S. application Ser. No. 11/343,747, assigned to the applicant of the present invention, and is incorporated herein by reference. In another embodiment, the present invention outputs data, through a wireless or wired network, to a central station that permits a single user to supervise the performance of multiple X-ray checkpoints.

In another embodiment, the present invention comprises a control panel that is protected from water and other contaminants using a clear plastic or glass cover. Furthermore, the control panel can include environmental indicators, such as temperature, humidity, and wind speed. Alternatively, such indicators can be located anywhere else on the system.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

The invention claimed is:

1. An imaging system having improved mobility, comprising:
   an X-ray source encased in a first enclosure;
   a conveyor belt assembly arranged to loop through said first enclosure;
   an electronics system for controlling the X-ray source and conveyor belt;
   a base frame positioned below said first enclosure, wherein said base frame comprises a connector for transporting the system;
   a beam attaching said first enclosure with said base frame; and
   a display device for presenting an image of an object to an operator.

2. The imaging system of claim 1 wherein said beam has a first part and a second part, wherein the first part extends outward from said first enclosure in parallel to the conveyor belt and the second part extends downward to the base frame, perpendicular to the conveyor belt.

3. The imaging system of claim 1 wherein said connector comprises a hook, slot, or hole.

4. The imaging system of claim 1 further comprising an environmental control system comprising a dehumidifier.

5. The imaging system of claim 1 further comprising an environmental control system comprising an internal cooling device.

6. The imaging system of claim 1 further comprising a protective casing comprising a first part adapted to attach to the base frame and cover a first end of the imaging system and a second part adapted to attach to the base frame and cover an opposing, second end of the imaging system.

7. The imaging system of claim 6 further comprising a plurality of eyelets positioned at corners of the protective casing.

8. The imaging system of claim 1 further comprising a plurality of fork tubes adapted to be received by a forklift.

9. The imaging system of claim 1 further comprising a second enclosure, wherein said electronics system is encased in the second enclosure.

10. The imaging system of claim 1 wherein the conveyor belt assembly is arranged to loop around an external underside of said first enclosure.

11. The X-ray imaging system of claim 1 further comprising a plurality of cleaning elements for removing contaminants from said conveyor belt, wherein said cleaning element is at least one of a brush, blower, cleaning pad, or ionizer.

12. The X-ray imaging system of claim 1 further comprising a sensor for sensing a temperature and a controller, wherein said controller controls the activation of said X-ray source or said electronics when said temperature sensed by said sensor exceeds a predetermined temperature.

* * * * *